United States Patent
Satou

(10) Patent No.: US 8,841,589 B2
(45) Date of Patent: Sep. 23, 2014

(54) CERAMIC HEATER AND GAS SENSOR ELEMENT

(75) Inventor: Chimato Satou, Inabe (JP)

(73) Assignee: Denso Corporation, Kariya (JP)

(*) Notice: Subject to any disclaimer, the term of this patent is extended or adjusted under 35 U.S.C. 154(b) by 261 days.

(21) Appl. No.: 13/597,938

(22) Filed: Aug. 29, 2012

(65) Prior Publication Data
US 2013/0048627 A1 Feb. 28, 2013

(30) Foreign Application Priority Data

Aug. 30, 2011 (JP) ................. 2011-187367

(51) Int. Cl.
| | | |
|---|---|---|
| H05B 3/03 | (2006.01) | |
| H05B 3/08 | (2006.01) | |
| H05B 3/12 | (2006.01) | |
| H05B 3/16 | (2006.01) | |
| G01N 27/409 | (2006.01) | |
| H05B 3/26 | (2006.01) | |
| H05B 3/06 | (2006.01) | |
| G01N 27/406 | (2006.01) | |
| G01N 27/407 | (2006.01) | |

(52) U.S. Cl.
CPC ............ *H05B 3/265* (2013.01); *G01N 27/4067* (2013.01); *G01N 27/407* (2013.01); *H05B 3/06* (2013.01); *H05B 3/12* (2013.01); *H05B 2203/003* (2013.01); *H05B 2203/013* (2013.01)
USPC ............ 219/541; 219/209; 219/552; 219/553

(58) Field of Classification Search
CPC .............. H05B 3/03; H05B 3/06; H05B 3/12; H05B 3/265; H05B 2203/003; H05B 2203/0013; G01N 27/4062; G01N 27/4067; G01N 27/407; G01N 27/4071
See application file for complete search history.

(56) References Cited

U.S. PATENT DOCUMENTS 4,883,947 A * 11/1989 Murase et al. ............ 219/553
4,952,903 A * 8/1990 Shibata et al. ............. 338/34
(Continued)

FOREIGN PATENT DOCUMENTS

| CN | 1387390 A | 12/2002 |
|---|---|---|
| JP | 03-149791 | 6/1991 |

(Continued)

OTHER PUBLICATIONS

Office Action (3 pages) dated Jul. 24, 2013, issued in corresponding Japanese Application No. 2011-187367 and English translation (3 pages).

(Continued)

*Primary Examiner* — Joseph M Pelham
(74) *Attorney, Agent, or Firm* — Nixon & Vanderhye PC

(57) ABSTRACT

A ceramic heater in which a heater pattern is formed on a ceramic substrate is disclosed. The heater pattern has a heating element and lead portions. The heating element has heating connection ends and the lead portions have lead connection ends. The heating element and the lead portions are connected at joints which are formed by overlaying the heating connection ends and the lead connection ends. The heater pattern, as viewed in a direction perpendicular to a plane in which the heater pattern is formed, has inwardly recessed concavities formed on both widthwise sides of each of the joints. The concavities include portions in each of which a profile of the respective heating connection end crosses a profile of the respective lead connection end.

9 Claims, 7 Drawing Sheets

(56) References Cited

U.S. PATENT DOCUMENTS

| | | | |
|---|---|---|---|
| 5,444,228 A * | 8/1995 | Gelus | 219/549 |
| 6,169,275 B1 | 1/2001 | Noda et al. | |
| 6,194,693 B1 | 2/2001 | Shirai et al. | |
| 7,427,911 B2 * | 9/2008 | Catchpole | 338/22 R |
| 7,947,933 B2 * | 5/2011 | Nagasako et al. | 219/544 |
| 2005/0160793 A1 * | 7/2005 | Schumann et al. | 73/31.05 |
| 2007/0114130 A1 * | 5/2007 | Lankheet et al. | 204/424 |
| 2013/0068754 A1 * | 3/2013 | Ptasienski et al. | 219/541 |

FOREIGN PATENT DOCUMENTS

| | | |
|---|---|---|
| JP | 05-182746 | 7/1993 |
| JP | 07-282960 | 10/1995 |
| JP | 08-148260 | 6/1996 |
| JP | 09-326538 | 12/1997 |
| JP | 10-001376 | 1/1998 |
| JP | 11-157920 | 6/1999 |
| JP | 2000-058237 | 2/2000 |
| JP | 2000-268944 | 9/2000 |
| JP | 2004-146356 | 5/2004 |
| JP | 2004-342622 | 12/2004 |
| JP | 2007-042615 | 2/2007 |
| JP | 2009-070819 | 4/2009 |
| JP | 2010-210134 | 9/2010 |

OTHER PUBLICATIONS

Office Action (10 pgs.) dated May 15, 2014 issued in corresponding Chinese Application No. 201210315386.6 with an at least partial English-language translation thereof (10 pgs.).

* cited by examiner

US 8,841,589 B2

CERAMIC HEATER AND GAS SENSOR ELEMENT

CROSS REFERENCE TO RELATED APPLICATION

This application is based upon and claims the benefit of priority from the prior Japanese Patent Application No. 2011-187367, filed Aug. 30, 2011, the entire content of which is incorporated herein by reference.

BACKGROUND OF THE INVENTION

1. Field of the Invention

The present invention relates to a gas sensor element and a ceramic heater to heat the gas sensor element.

2. Description of the Related Art

A gas sensor is provided in an exhaust gas system of a vehicle internal combustion engine. The gas sensor detects a concentration of a specific gas contained in a gas to be measured such as an exhaust gas. The gas sensor has a built-in ceramic heater for heating a gas sensor element.

For example, there is a ceramic heater having a heater pattern formed on a surface of a ceramic substrate. The heater pattern has a heating element that generates heat when a current is passed therethrough and a lead portion that conducts electricity to the heating element.

Recently, there is a tendency to reduce the specific resistance of heating elements, since gas sensor elements are required, for example, to warm up rapidly (early-activation) and to be used, under high temperature.

For example, JP-A-2004-342622 discloses a ceramic heater. The ceramic heater is configured such that the heating element and the lead portion are made of a different material, and that the heating element has lower specific resistance than the lead portion. In this ceramic heater, since the heating element, and the lead portion, are made of a different material, the end of the heating element and the end of the lead portion are overlaid with each other, for example, thereby joining the heating element and the lead portion.

SUMMARY OF THE INVENTION

However, the above-mentioned ceramic heater has the fallowing issues.

That is, the heating element and the lead portion are made of a different material. Therefore, when, conducting electricity to the ceramic heater, stress is likely to be imposed on the joint between the heating element and the lead portion due to the difference in linear expansion between, the heating element and the lead portion, causing cracks starting from the joint. As the gas sensor element, is more required to warm up rapidly (early-activation) and to be used under high, temperature, this issue becomes more serious.

For example, when manufacturing the ceramic heater, a conductive paste for forming the heating element and a conductive paste for forming the lead portion are printed on a surface of the ceramic substrate. At the joint between the heating element and the lead portion, the conductive paste for forming the heating element and the conductive paste for forming the lead portion are printed being overlaid with each other. Therefore, spreading is likely to occur in one conductive paste portion printed being overlaid on top of the other and spread peripherally, causing a short circuit in the ceramic heater.

As mentioned above, the heating element and the lead portion are made of a different material. Therefore, when firing the conductive pastes, stress is likely to be imposed on the joint between the heating element and the lead portion due to the difference in contraction coefficient between the two. As a result, cracks may be caused in the heater pattern and the ceramic substrate starting from the joint.

The present invention has been achieved in light of the above-described issues. An object of the present invention is to provide a ceramic heater having excellent durability and enabling prevention of a short circuit, and a gas sensor element.

According to one aspect of the present invention, there is provided a ceramic heater in which a heater pattern is formed on a ceramic substrate, the heater pattern having a heating element that generates heat when a current is passed therethrough and lead portions that conduct electricity to the heating element, wherein: the heating element has heating connection ends connected to the respective lead portions; the lead portions have lead connection ends connected to the heating connection ends of the heating element; the heating element and the lead portions are connected at joints, the joints being formed by overlaying the heating connection ends and the lead connection ends; and the heater pattern formed on the ceramic substrate, as viewed in a direction perpendicular to a plane in which the heater pattern is formed, has inwardly recessed concavities formed on both widthwise sides of each of the joints, the concavities including portions in each of which a profile of the respective beating connection end crosses a profile of the respective lead connection end.

According to a further aspect of the present invention, there is provided a gas sensor element having the ceramic heater according to the above first aspect.

DETAILED DESCRIPTION OF THE PREFERRED EMBODIMENTS

Figure 1:
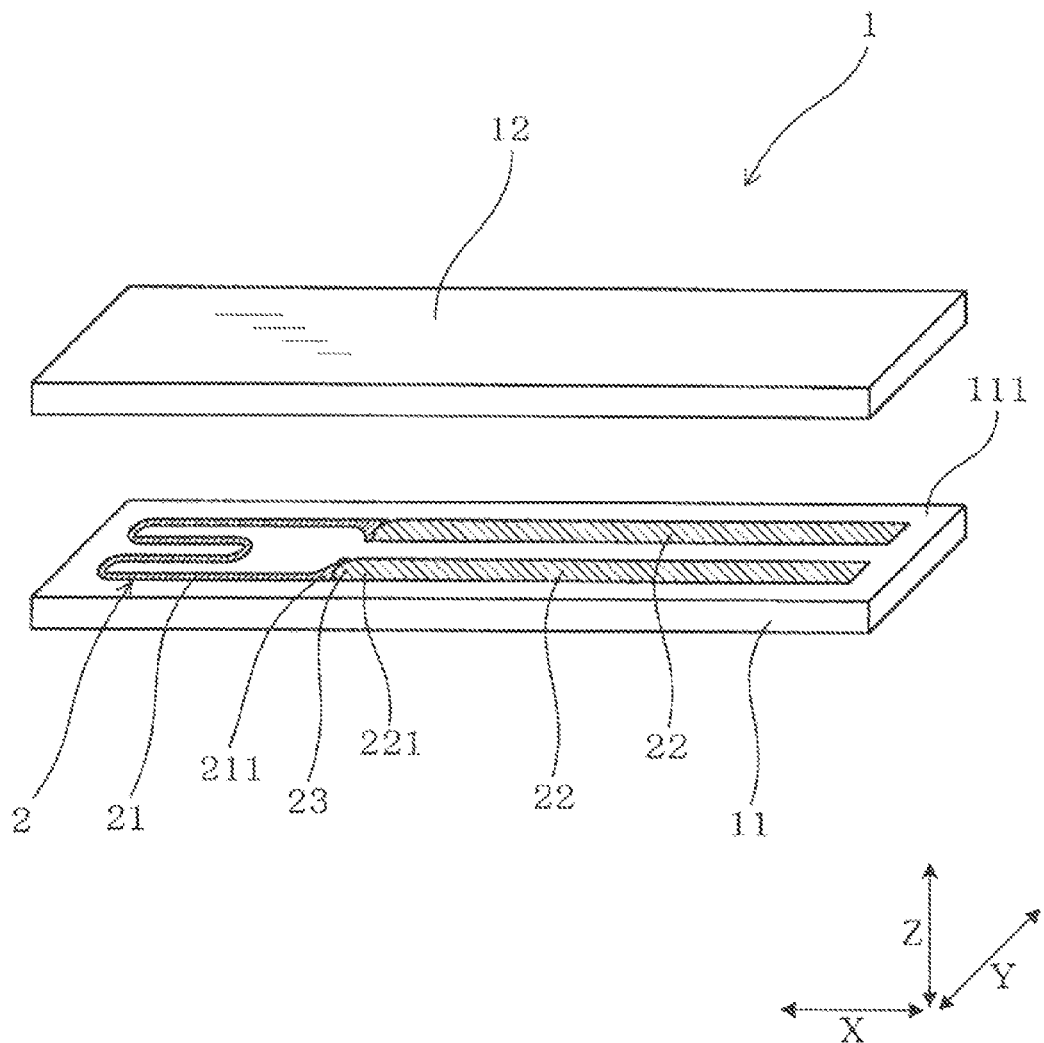
FIG. 1 is an explanatory view showing a structure of the ceramic heater according to a first example of the present invention.

A ceramic heater and a gas sensor element according to preferred embodiments of the present invention will hereinafter be described with reference to the drawings.

In the ceramic heater, a heating element and lead portion are connected at a joint which is formed by overlaying the heating connection end and the lead connection end. More specifically, the joint may be formed by overlaying a lead connection end of a lead portion on top of a heating connection end of a heating element, or vice versa.

The heater pattern formed on the ceramic substrate, as viewed in a direction perpendicular to a plane in which the heater pattern is formed, has inwardly recessed concavities formed on both widthwise sides of each of the joints. The concavities include portions in each of which a profile of the respective heating connection end crosses a profile of the respective lead connection end.

According to this, it may provide a ceramic heater having excellent durability and enabling prevention of a short circuit.

On both sides of the joints between the heating element and the lead portions, stress may be generated easily by energization of the ceramic healer. Therefore, concavities, in each of which the side face of the heater pattern is dented inward, are formed on both widthwise sides of each of the joints. The concavities allow distribution and alleviation of the stress occurring at the joints. As a result, it may reduce cracking which occurs in the ceramic substrate and starts at the joints, thereby enhancing the durability of the ceramic heater.

When manufacturing the ceramic heater, for example, a conductive paste for forming the heating element and a conductive paste for forming the lead portions are printed on a surface of the ceramic substrate. At each joint between the heating element and the lead portion, the conductive paste for forming the heating element and the conductive paste for forming the lead portion are overlaid, with each other, thereby printing the heating element and the lead, portion with high accuracy. That is, even when sagging occurs in one conductive paste printed being overlaid on top of the other, the sagging can be immobilized within the concavities formed on both width-wise sides of each of the joints. As the result, peripheral spread of the sagging is suppressed. This prevents occurrence of short circuit in the ceramic heater.

On both widthwise sides of each of the joints between, the heating element and the lead portions, stress may be generated easily at the firing of the conductive pastes printed on the ceramic substrate. Therefore, concavities, in each of which the side face of the heater pattern is dented inward, are formed on both widthwise sides of each of the joints. The concavities allow distribution and alleviation of the stress occurring at the joints. As a result, it may reduce cracking in the ceramic substrate and starts at the joints, thereby enhancing the durability of the ceramic heater.

In the heater pattern, at least either the heating connection ends of the heating element or the lead connection ends of the lead portions preferably have an edge having an arc-shaped curve.

It may distribute and alleviate the stress generated in the joints between the heating element and the lead portions by energization of the ceramic heater. Similar effects can be expected at the firing. It may further reduce the crack which occurs in the ceramic substrate and starts at the joints.

A relation of $R1 \leq R2$ is preferably realized, where R1 is a resistance in a joint region, the joint region extending from a tip end of each heating connection end and having a length L, and R2 is a resistance in a lead region, the lead region extending from, the tip end of the heating connection end toward the corresponding lead portion and having a length equal to the length L.

Excellent exothermic characteristic by energisation, can be obtained, thereby enabling rapid warm-up (early-activation) of the gas sensor element. Further, it may prevent abnormal heat generation at joints and occurrence of the crack starting at the joints.

When the relation of $R1 > R2$ is realized, excellent exothermic characteristic by energisation is unlikely to be obtained. Since heat is abnormally generated at joints between the heating element and the lead portions, crack may be caused, starting from the joints.

At least either the heating connection ends of the heating element or the lead connection ends of the lead portion preferably have an edge having a convex part which projects from the edge toward the long direction of the heater pattern.

In manufacturing the ceramic heater, even when there is an offset in a formation position, of the heating element and the lead portions in the long direction, it may secure a sufficient joint area between the heating element and the lead portions. As a result, it may prevent abnormal generation of heat at joints and occurrence of the crack starting at the joints.

When length of the convex parts in the long direction is "S" and length, of the joints in the long direction excluding the convex parts is "M".

a relation of $S = a \times M + b$ is preferably realized, where "a" preferably ranges from 0.3 mm. to 5.0 mm, and "b" preferably ranges from 0.0 mm to 0.2 mm.

In manufacturing the ceramic heater, even when there is an offset in a formation position of the heating element and the lead portions in the long direction, it may secure a more sufficient joint area between the heating element and the lead portions.

hi the relation of $S = a \times M + b$, when "a" is less than 0.3, a sufficient joint area is unlikely to be secured between the healing element and the lead portions, when there is an offset in a formation position of the heating element and the lead portions in the long direction in manufacturing the ceramic heater. When "a" is more than 0.5, the joint area becomes larger than necessary, and thus manufacturing cost may be increased.

When "b" is more than 0.2, the joint area becomes larger than necessary, and thus manufacturing cost may be increased.

The joints are preferably formed by overlaying the lead connection ends of the lead portions on top of the respective heating connection ends of the heating element, and the width of the lead connection ends Is preferably smaller than that of the heating connection ends.

This may facilitate accurate overlaying the lead connection ends of the lead portions on top of the respective heating connection ends of the heating element, in forming the heater pattern by printing conductive pastes on the ceramic substrate.

Even when sagging or bleeding of the conductive paste occurs in the lead connection ends of the lead portions printed being overlaid on top, it may suppress the sagging or bleeding from extending beyond the heating connection ends of the heating element. As a result, it may prevent occurrence of a short circuit in the ceramic heater.

The heating element is preferably made of materials of which a main component is at least one of or a combination of a plurality of metals selected from platinum, gold, palladium and rhenium. At least one of or a combination of a plurality of materials selected from alumina, zirconia and titania in a total amount of 11 to 14 parts by weight Is preferably included in 100 parts by weight of the main component.

Thus, excellent exothermic characteristic by energization can be obtained, thereby enabling rapid warm-up (early-activation) of the gas sensor element. In addition, excellent sinterability can be obtained at the firing.

With respect to the heating element, in the case where content of at least one of or a combination of a plurality of materials selected from alumina, sarcoma and titania is less than an amount of 11 to 14 parts by weight, sinterability when firing may be deteriorated, thereby causing peeling or cracking. On the contrary, in the case where content of at least one of or a combination of a plurality of materials selected from alumina, zirconia and titania is more than an amount of 10 parts by weight, excellent exothermic characteristics during energization are unlikely to be obtained.

The pair of lead portions preferably contains, as a main component, at least one of or a combination of a plurality of metals selected from platinum, gold, palladium and rhenium. Further, at least one of or a combination of a plurality of materials selected from alumina, zirconia and titania in an amount of 7 to 10 parts by weight is preferably included in 100 parts by weight of the main component.

Thus, excellent exothermic characteristic by energization can be obtained, thereby enabling rapid warm-up (early-activation) of the gas sensor element. In addition, excellent sinterability can be obtained at the firing.

With respect to the pair of the lead portions, in the case where content of at least one of or a combination of a plurality of materials selected from alumina, zirconia and titania is less than an amount of 7 parts by weight, sinterability may be deteriorated at the firing, thereby causing peeling or crack. On the contrary, in the case where content of at least one of or a combination of a plurality of materials selected from, alumina, sarcoma and titania is more than an amount of 10 parts by weight, excellent exothermic characteristics are unlikely to be obtained, when the ceramic heater is energized.

The heater pattern is preferably formed by printing using conductive pastes.

At the joints between the heating element and the lead portions, since sagging in printing the conductive paste can be suppressed, the above-described effect of preventing the occurrence of short circuit in the ceramic heater can be exerted effectively.

The gas sensor element according to embodiments of the present invention has a ceramic heater having excellent durability and enabling prevention of a short circuit.

According to this, a gas sensor element having excellent durability and enabling prevention of a short circuit can be obtained.

Applications of the above gas sensor element include: an A/F sensor element incorporated in a A/F sensor element which is used for an exhaust gas feedback system in an exhaust pipe of an internal-combustion engine for various vehicles, such as an automobile engine ; an oxygen sensor element that detects the oxygen concentration included in the exhaust gas; and a NOx sensor element used for detecting deterioration, for example, of a three-way catalyst provided in an exhaust pipe, i.e. used for detecting the concentration of the air-polluting substances, such as NOx.

EXAMPLE 1

A ceramic heater and a gas sensor element according to an example 1 are described with reference to the drawings. As shown in FIGS. 1 to 4, a ceramic heater 1 according to the example 1 has a ceramic substrate 11 and a heater pattern 2 formed on the ceramic substrate 11. The heater pattern 2 includes a heating element 21 that generates heat when a current is passed therethrough and a pair of lead portions 22 that conducts electricity to the heating element 21.

The heating element 21 has a pair of heating connection ends 211 connected to the pair of lead, portions 22, The pair of lead portions 22 has lead connection ends 221 connected to the pair of heating connection ends 211 of the heating element 21. The heating element 21 and the lead portions 22 are connected at joints 23. The joints 23 are formed by overlaying the heating connection ends 211 and the lead connection ends 211.

The heater pattern 2 formed on the ceramic substrate 11 as viewed from a direction perpendicular to the plane in which the heater pattern 2 is formed, has inwardly dented concavities 24 formed on both widthwise sides of each of the joints 23. The concavities 24 include portions in each of which a profile of the heating connection end 211 crosses a profile of the lead connection end 221.

In the present example 1, the long direction, the width direction and the thickness direction of the ceramic substrate 11 are referred, to as a "long direction X", a "width direction Y" and a "thickness direction Y", respectively. The long direction, the width direction and the thickness direction of the beater pattern 2 (the heating element 21 and the lead portion 22) coincide with the long direction X, the width direction Y and the thickness direction Y, respectively, of the ceramic substrate mentioned above.

Figure 5:
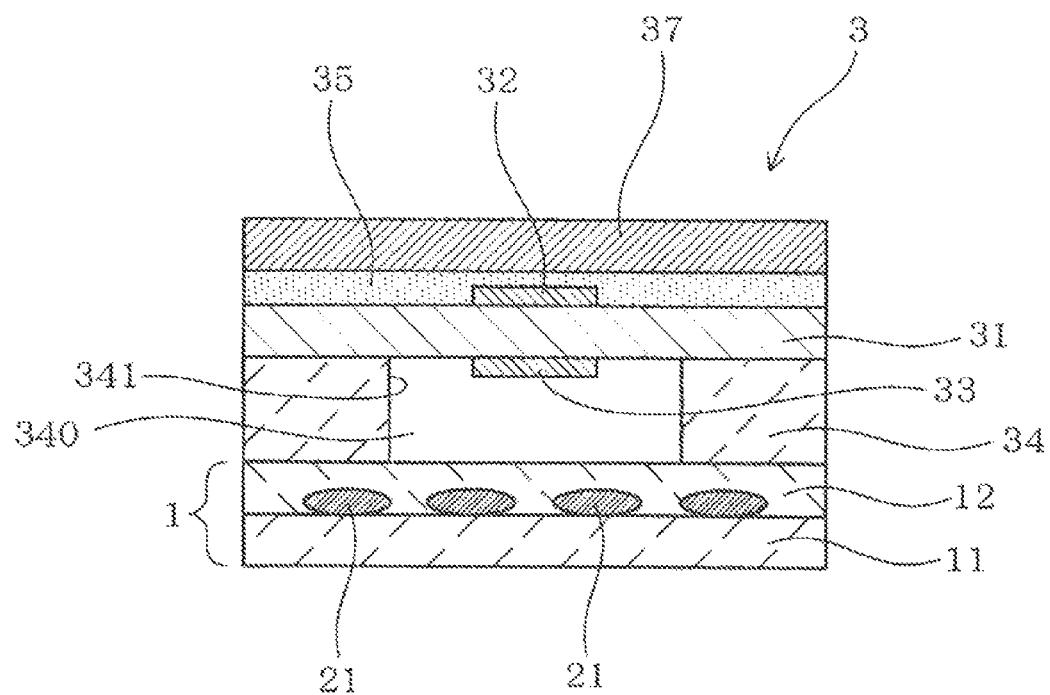
FIG. 5 is a cross-sectional view showing a structure of the gas sensor element according to a first example of the present invention.
Figure 6:
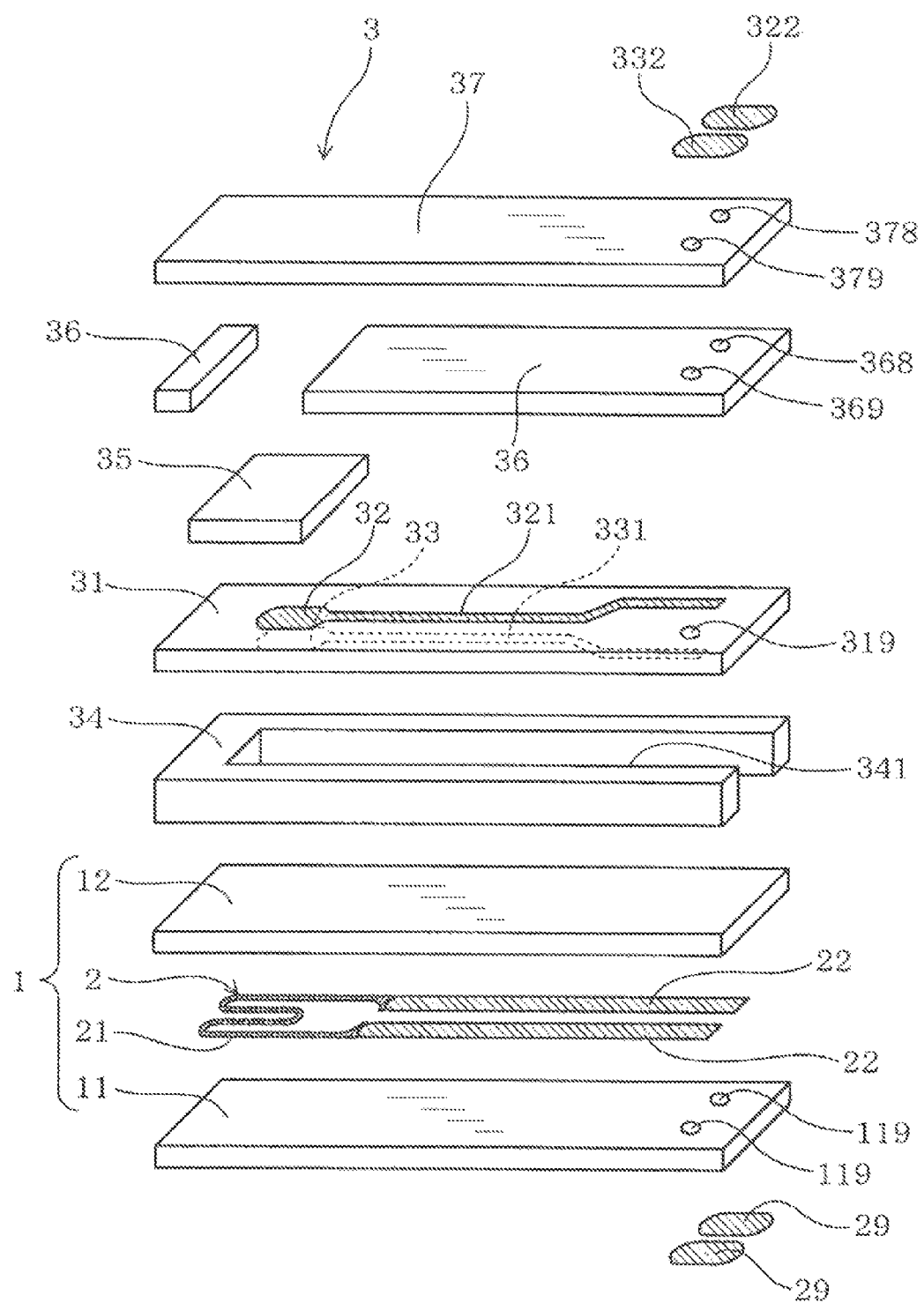
FIG. 6 is an exploded perspective view showing a structure of the gas sensor element according to a first example of the present invention.

As shown, in FIGS. 5 and 6, the ceramic heater 1 according to the first example is located in a gas sensor element 3. The gas sensor element 3 has a solid electrolyte body 31 having oxygen ion conductivity. The solid electrolyte body 31 is made of materials of which the main component is zirconia. On one side of the solid electrolyte body 31, a measuring electrode 32 is provided. On the other side of the solid electrolyte body 31, a reference electrode 33 is provided. The measuring electrode 32 and the reference electrode 33 are made of materials of which the main component is platinum.

The outer side of the measuring electrode 32 is sequentially overlaid by a diffusion resistance layer 35 and a spacer layer 36. The diffusion resistance layer 35 is made of porous alumina having gas-permeability. The diffusion resistance layer 35 is configured to introduce a gas to be measured (exhaust gas) and bring the gas into contact with the measuring electrode 32. The spacer layer 36 is made of dense alumina having electrical insulation properties and gas-impermeability. The outer side of the spacer layer 36 is overlaid by a protective layer 37. The protective layer 37 is made of dense alumina having electrical insulation and gas-impermeability.

The outer side of the reference electrode 33 is overlaid by a reference gas chamber forming layer 34. The reference gas chamber forming layer 34 is made of dense alumina having electrical insulation and gas-impermeability. The reference gas chamber forming layer 34 has a notched portion 341 in which a reference gas chamber 340 is formed. The reference gas chamber 340 is configured to introduce a reference gas (air) and bring the reference gas into contact with the reference electrode 33.

Further, the outer side of the reference gas chamber forming layer 34 is overlaid by the ceramic heater 1.

The measuring electrode 32 Is electrically connected to a pair of electrode pads 322 via an electrically conductive connecting lead 321 and through-holes 368 and 378. These through-holes 368 and 378 are formed in the spacer layer 36 and the sheltered layer 37, respectively. Inside these through-holes 368 and 378, a conductor (not shown) is arranged.

The reference electrode 33 is electrically connected to a pair of electrode pads 332 via an electrically conductive connecting lead 331 and through-holes 319, 369 and 379. These through-holes 319, 369 and 379 are formed in the solid electrolyte body 31, the spacer layer 36 and the sheltered layer 37, respectively. Inside these through-holes 319, 369 and 379, a conductor (not shown) is arranged.

Next, details of the ceramic heater 1 are described.

As shown in FIG. 1, the ceramic heater 1 is configured to be overlaid by the ceramic substrate 11 and a ceramic insulating layer 12 (see FIG. 5), The ceramic insulating layer 12 is arranged between the ceramic substrate 11 and the reference gas chamber forming layer 34. The ceramic substrate 11 and the ceramic insulating layer 12 are made of dense alumina having electrical insulation and gas-impermeability.

Figure 2:
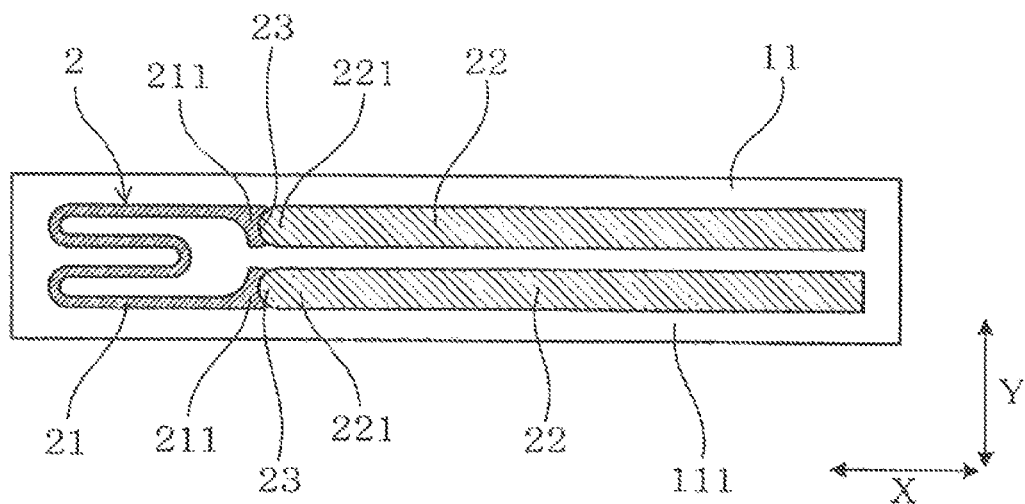
FIG. 2 is a top view circuit showing a heater pattern formed on a surface of the ceramic substrate according to a first example of the present invention.

As shown in FIGS. 1 and 2, the heater pattern 2 is formed on one surface ill of the ceramic substrate 11 so as to face the ceramic insulating layer 12. The heater pattern 2 is formed by printing conductive pastes.

The heater pattern 2 has the heating element 21 and the pair of lead portions 22. The heating element 21 generates heat by energisation and heats the gas sensor element 3 until the activation temperature is reached. The pair of lead portions 22 conducts electricity to the heating element 21.

The heating element 21 is made of materials of which the main component is platinum. The heating element 21 also contains alumina as a component other than the main component. Alumina in an amount of 11 to 14 parts by weight is included in 100 parts by weight of the platinum.

The pair of lead portions 22 is made of materials of which the main component is platinum. The lead portions 22 also contain alumina as a component other than the main component. Alumina in an amount of 7 to 10 parts by weight is included in 100 parts by weight of the platinum.

The heating element 21 is formed at one end of the ceramic substrate 11 id the long direction X, The heating element 21 has the heating connection ends 211 which are connected to the respective lead portions 22.

The lead portions 22 are formed in the long direction X of the ceramic substrate 11 so as to be in parallel with, each other in the width direction Y of the ceramic substrate 11. The lead, portions 22 have respective ends on one side, which serve as the heating connection ends 221 for establishing connection with the respective heating connection ends 211 of the heating element 21.

Figure 3:
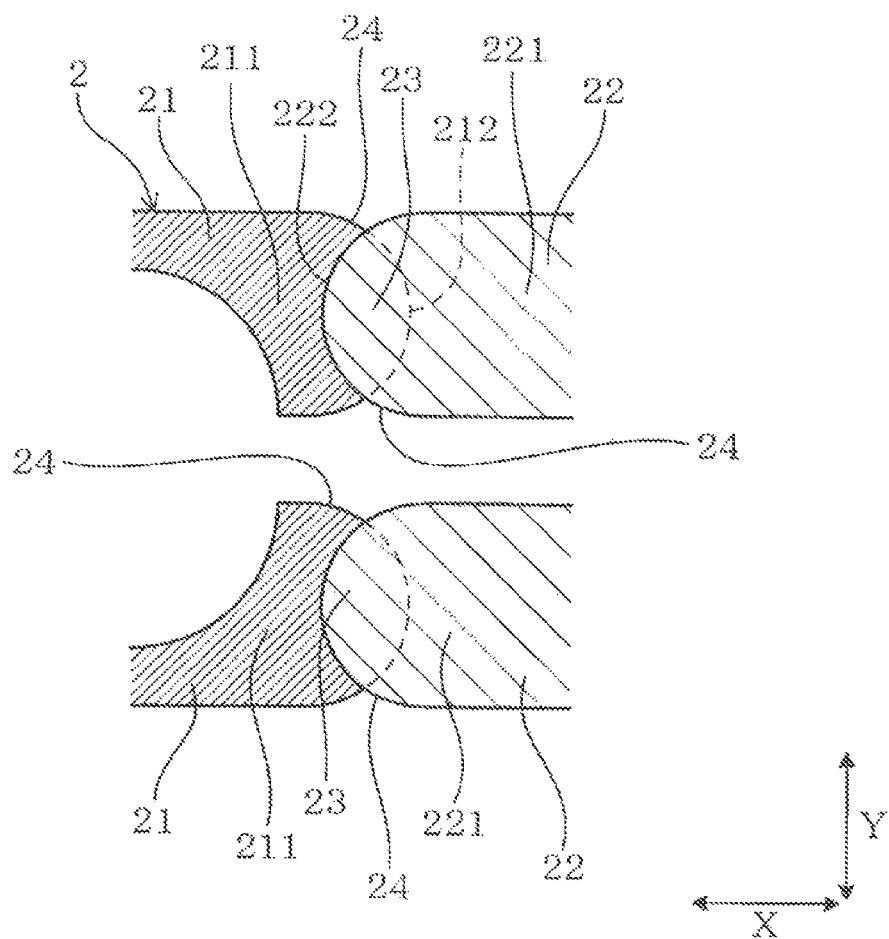
FIG. 3 is an enlarged view showing the joint between the heating element and the lead portion according to a first example of the present invention.
Figure 4:
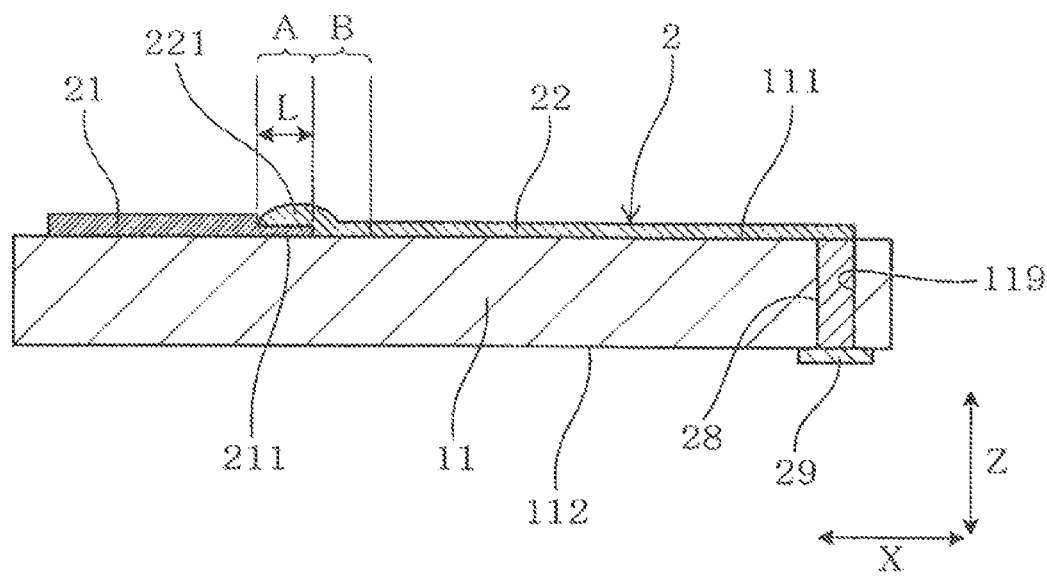
FIG. 4 is a cross-sectional view in the width direction of the ceramic substrate according to a first example between the present invention.

As shown in FIGS. 3 and 4, the heating element 21 and the lead portions 22 are connected at the pair of joints 23. The joints 23 are each formed by overlaying the heating connection end 211 of the heating element 21 and the lead connection end 221 of the lead portion 22 with each other. In the present embodiment, the joints 23 are each formed so that the lead connection end 221 of the lead portion 22 is overlaid on top of the heating connection end 211 of the heating element 21.

FIG. 3 shows the heater pattern 2 as viewed from the direction (the thickness direction Z) perpendicular to the surface 111 of the ceramic substrate 11, on which the heater pattern 2 is formed. As shown in FIG. 3, the heating connection end 211 of the heating element 21 and the lead connection end 221 of the lead portion 22 have edges 212, 222, respectively, having an arc-shaped curve.

The heater pattern 2 has inwardly dented, concavities 24 formed on both widthwise (width direction Y) sides of each of the joints 23. The concavities 24 include portions in each of which a profile of the heating connection end 211 crosses a profile of the lead connection end 221.

As shown in FIG. 4, the heater pattern 2 includes a joint region A having a length L in the long direction X. The joint region A extends from a tip end of the lead connection end 221 to a tip end of the heating connection end 211. The heater pattern 2 also includes a lead region B having the length L in the long direction X. The lead region B extends from the tip end of the lead connection end 211 toward the lead portion 22.

When resistance in the joint region A is "R1" and the resistance in the lead region B is "R2", a relation of R1≤R2 is realized.

The heating element 21 formed on the surface of the ceramic substrate 11 is electrically connected to a pair of electrode pads 29 provided on the other surface 112 of the ceramic substrate 11, via the pair of lead portions 22 and a pair of through-holes 119 formed, in the ceramic substrate 11. Inside each of the through-holes 119, a conductor 28 is arranged.

[Method for Manufacturing a Ceramic Heater 1 and a Gas Sensor Element 3]

A method for manufacturing the ceramic heater 1 and the gas sensor element 3 according to the preferred embodiments of the present invention will hereinafter be described.

Firsts alumina sheets fur forming the ceramic substrate 11 and the ceramic insulating layer 12 are formed, which construct the ceramic heater 1. In the alumina sheet for forming the ceramic substrate 11, the through-holes 119 are formed beforehand.

For example, this alumina sheet is formed as follows. First, slurry is prepared by mixing sintering additives, such as $SiO_2$, MgO or CaO, and an organic hinder into an alumina powder. Then, the slurry is shaped so as to have a thickness of 50 μm to 100 μm. such, as by doctor blade method to thereby obtain the alumina sheet.

Then, conductive pastes for forming the hearer pattern 2 are printed on one surface of the alumina, sheet that serves as the ceramic substrate 11. Specifically, after a conductive paste for forming the heating element 21 is printed on the alumina sheet, a conductive paste for forming the lead portions 22 is printed. At the joints 23 in which the heating element 21 and the lead portions 22 are joined, the conductive paste for forming the lead portions 22 is printed on top of the conductive paste for forming the heating element 21.

The conductive paste for forming the heating element 21 is prepared by mixing the following materials. The materials include a platinum powder as a main component, an alumina powder in an amount of 12 parts by weight in 100 parts by weight of the platinum powder, an organic binder, such as acrylic resin, a plasticizer, such as DBF or DOP, and an organic solvent, such as α-terpineol.

The conductive paste for forming the lead portions 22 is prepared by mixing the following materials. The materials include a platinum powder as a main component, an alumina powder in an amount of 9 parts by weight in 100 parts by weight of the platinum powder, an organic binder, such as acrylic resin, a plasticizer, such as DBP or DOP, and an organic solvent, such as α-terpineol.

On the surface 112 of the alumina sheet that serves as the ceramic substrate 11, a conductive paste for forming the electrode pads 29 is printed. Also, a conductive paste for forming the conductor 28 is filled in the through-holes 119 formed beforehand. Then, a heater laminated body is formed by laminating the alumina sheet of the ceramic substrate 11 and the alumina sheet of the ceramic insulating layer 12.

Further, a zirconia sheet for forming the solid electrolyte body 3 is formed. Then, on the zirconia sheet, conductive pastes for forming the measuring electrode 32, the reference electrode 33 and the like are printed. Further, alumina sheets for forming the reference gas chamber forming layer 34, the diffusion resistance layer 35, the spacer layer 36 and the sheltered layer 37 are prepared. Then, these alumina sheets are laminated to obtain a sensor laminated body.

After that, the heater laminated body is located on top of the sensor laminated body, followed by thermocompression of the entirety, thereby forming an element laminated body. The obtained element laminated body is fired under predetermined conditions. As a result, the gas sensor element 3 (see FIG. 5) of the present embodiment is obtained, with the ceramic heater 1 (see FIGS. 1 to 4) being incorporated therein.

Next, function and effect of the ceramic heater 1 and the gas sensor element 3 (see FIG. 5) according to the present embodiment will be described.

In the ceramic heater 1 according to the present embodiment, the heating element 21 and the lead portions 22 are joined, at the joints 23 in which the lead connection ends 211 and the respective lead connection ends 221 are overlaid. The heater pattern 2 has the inwardly dented concavities 24 formed on both widthwise (width direction Y) sides of each of the joints 23. The concavities 24 include portions in each of which a profile of the heating connection end 211 crosses a profile of the lead connection end 221.

This configuration provides the ceramic heater 1 having excellent durability and enabling prevention of a short circuit.

On both of widthwise sides of each of the joints 23 between the heating element 21 and the lead portions 22, stress may be generated easily by energization of the ceramic heater 1. In this regard, in the present embodiment, the concavities 24, in each of which a side face of the heater pattern 2 is dented inward, are formed on the respective widthwise sides of each of the joints 23. When current is passed through the ceramic heater 1, the concavities 24 are able to effectively distribute and alleviate the stress occurring at the joints 23. As a result, it is possible to reduce cracking in the ceramic substrate 11 and which starts at the joints 23, thereby enhancing the durability of the ceramic heater 1.

When manufacturing the ceramic heater 1, the heater pattern 2 is produced by printing a conductive paste for forming the heating element 21 and a conductive paste for forming the lead portion 22 on a surface of the ceramic substrate 11. The heater pattern 2 has the joints 23 in each of which the lead connection end 211 of the heating element 21 and the lead connection end 221 of the lead portion 22 are printed being overlaid with each other. In the present embodiment, the heating element 21 and the lead portion 22 can be printed by highly accurately overlaying the ends 211 and 221 with each other. That is, even when sagging occurs in one conductive paste printed on tap of the other, the sagging remains inside the concavities 24 formed on both widthwise sides of each of the joints 23, and is immobilized, thereby preventing peripheral spread of the sagging. As a result, it is possible to prevent the occurrence of short circuit in the ceramic heater 1.

On both widthwise sides of each of the joints 23 between the heating element 21 and the lead portion 22, stress may be generated easily in firing the conductive pastes printed on the ceramic substrate 1. In this regard, in the present embodiment, the concavities 24 formed on both of the widthwise sides of each of the joints 23 are able to distribute and alleviate the stress occurring at the joints 23. As a result, it is possible to reduce cracking which occurs in the heater pattern 2 or the ceramic substrate H and starts at the joints 23, thereby enhancing the durability of the ceramic heater 1.

In the ceramic heater 1, the heating connection end 211 of the heating element 21 and the lead connection end 221 of the lead portion 22 have the edges 212, 222, respectively, having an arc-shaped curve. With this configuration, when the ceramic heater 1 is energized, it may further distribute and alleviate the stress occurring at the joint 23 between the heating element 21 and each, lead portion 22. Similar effect can be expected at the firing. As a result, it may further reduce the occurrence of the crack starting at the joints 23.

When resistance In the joint region A of the heater pattern 2 is "R1" and resistance in the lead region B is "R2", a relation of R1≤R2 is realized. As a result, when the ceramic heater 1 is energized, excellent exothermic, characteristic can be obtained thereby enabling rapid warm-up (early-activation) of the gas sensor element 3. In addition, it may prevent abnormal generation of heat at the joints 23 and the occurrence of the crack starting at the joints 23.

The heating element 21 is mode of materials of which the main component is platinum. The materials also include alumina as a component other than the main component. Alumina in an amount of 11 to 14 parts by weight is included in 100 parts by weight of the platinum. The pair of lead portions 22 is made of materials of which the main component is platinum. The materials also include alumina as a component other than the main component. Alumina in an amount of 7 to 10 parts by weight is included in 100 parts by weight of the platinum.

As a result, when the ceramic heater 1 is energized, excellent exothermic characteristic can be obtained thereby enabling rapid warm-up (early-activation) of the gas sensor element 3. Further, excellent sinterability can be obtained at the firing.

The heater pattern 2 is formed by printing a conductive paste for forming the heating element 21 and a conductive paste for forming the lead portions 22. As a result, it is possible to suppress the occurrence of sagging, thereby preventing creation of a short circuit in the ceramic heater 1.

The gas sensor 3 according to the present example has the built-in ceramic heater 1 having excellent durability and enabling prevention of a short circuit. Thus, the gas sensor 3 having excellent durability and reliability can be obtained.

EXAMPLE 2

A ceramic heater 1 according to a second example is described with reference to the FIGS. 7 to 9. In the second and the subsequent examples, the components identical with or similar to those in the first example are given, the same reference numerals for the sake of omitting unnecessary explanation.

The second example is different from the first example in that the structure of the heating element 21 and the lead portions 22 in the heater pattern 2 has been changed.

Figure 7:
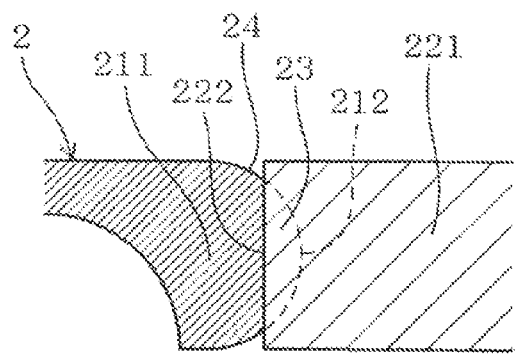
FIG. 7 is an enlarged view showing the joint between the heating element and the lead portion, according to a second example of the present invention.
Figure 7:
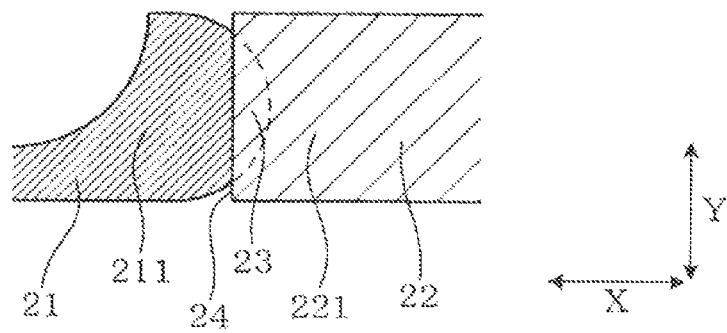

In the example of the heater pattern 2 shown in FIG. 7, the heating connection end 211 of the heating element 21 has the edge 212 having an arc-shaped curve. On the other hand, the lead connection end 221 of the lead portion 22 has the edge 222 which is straight and parallel to the width direction Y.

Figure 8:
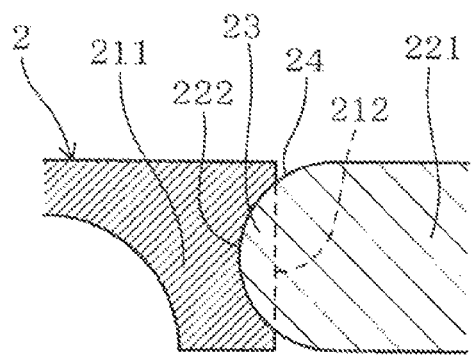
FIG. 8 is an enlarged view showing the joint between the heating element and the lead portion according to a second example of the present invention.
Figure 8:
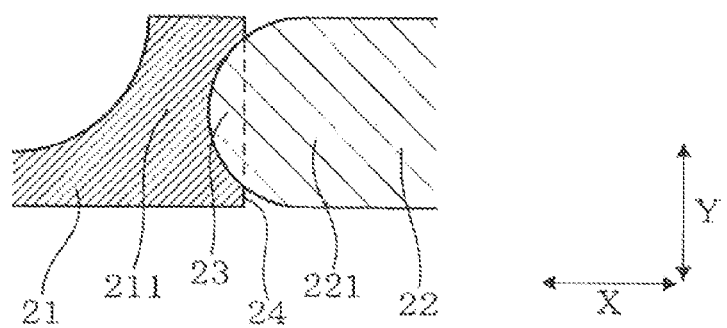

In the example of the heater pattern 2 shown in FIG. 8, the heating connection end 211 of the heating element 21 has the edge 212 which is straight and parallel to the width direction Y. On the other hand, the lead connection end 221 of the lead portion 22 has the edge 222 having an arc-shaped curve.

Figure 9:
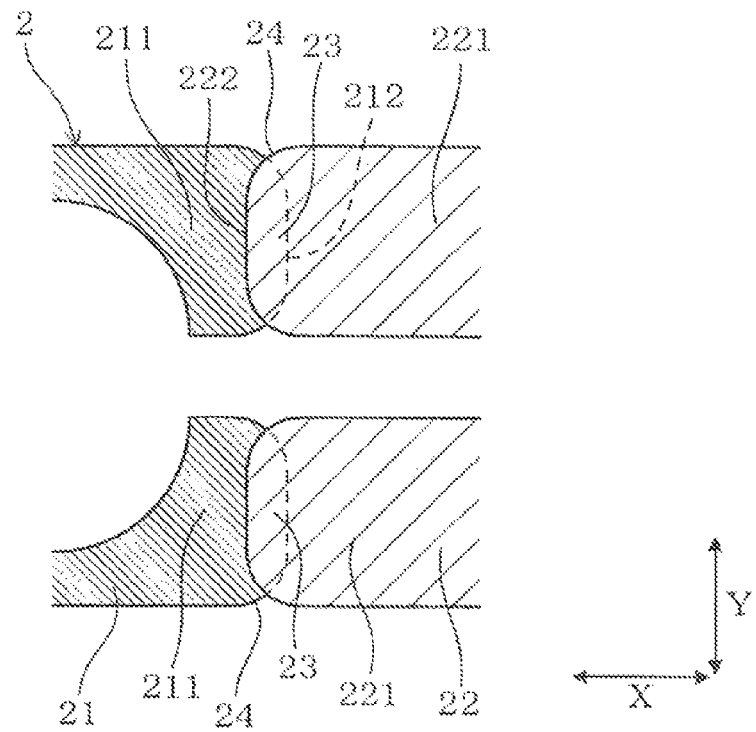
FIG. 9 is an enlarged view showing the joint between the heating element and the lead portion according to a second example of the present invention.

In the example of the heater pattern 2 shown in FIG. 9, the heating connection end 211 of the heating element 21 has the edge 212 which is composed of a straight portion parallel to the width direction Y, and arc-shaped curve portions at both ends of the straight portion. Also, the lead connection end 221 of the lead portion 22 has the edge 222 having the same shape as that of the edge 212.

Figure 10:
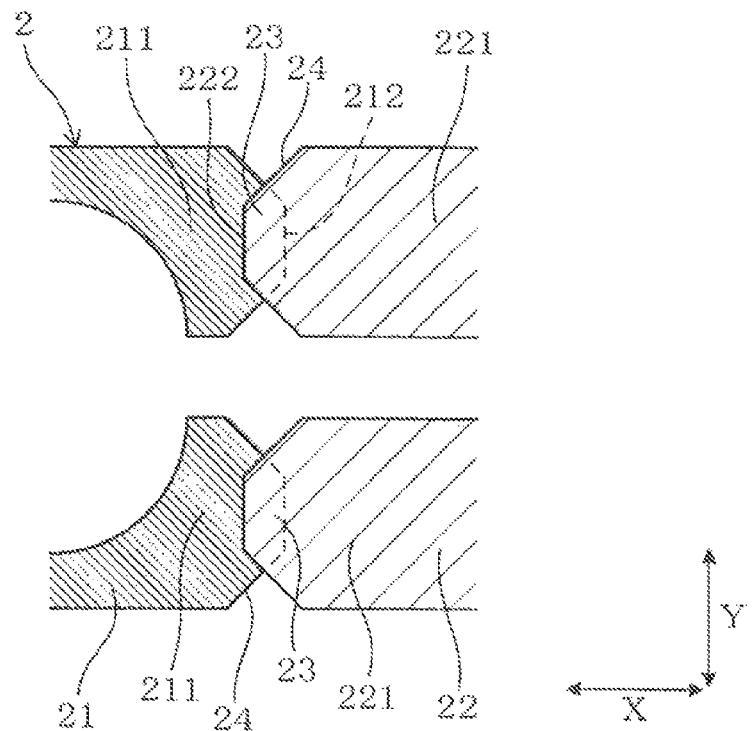
FIG. 10 is an enlarged view showing the joint between the heating element and the lead portion according to a second example of the present invention.

In the example of the heater pattern 2 shown in FIG. 10, the heating connection end 211 of the heating element 21 has the edge 212 which is composed of a straight portion parallel to the width direction Y and obliquely straight portions at both ends of the straight portion. Also, the lead connection end 221 of the lead portion 22 has the edge 222 having the same shape as that of the edge 212.

In any of the ceramic heaters shown in FIGS. 7 to 10, the configurations, functions and effects are similar to those of the ceramic heater 1 according to the first example. Therefore, the description is omitted.

EXAMPLE 3

The ceramic heater 1 according to a third example is described with reference to FIG. 11.

The third example is different from the first example in that the structure of the heating element 21 and the lead portions 22 in the heater pattern 2 has been changed from the first example.

Figure 11:
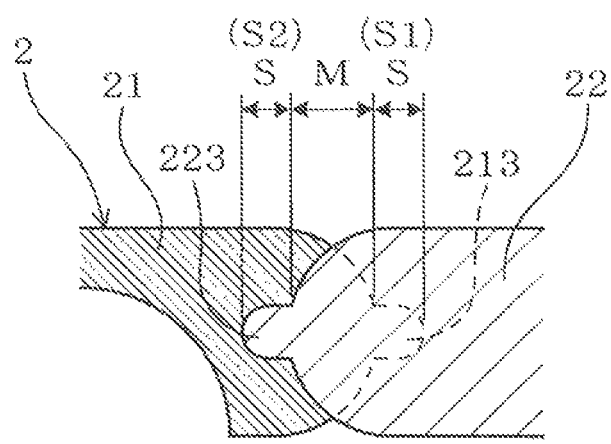
FIG. 11 is an enlarged view showing the joint between the heating element and the lead portion according to a third example of the present invention.
Figure 11:
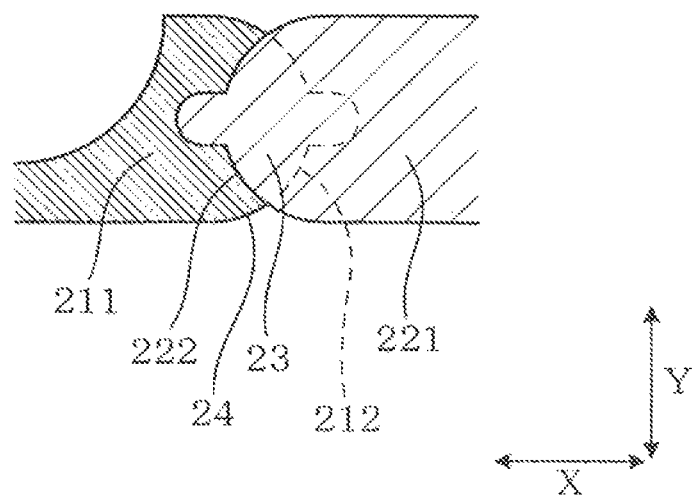

As shown in FIG. 11, the heating connection end 211 of the heating element 21 has the edge 212 having a convex part 213 which projects from the edge 212 in the long direction X. The convex part 213 is formed so as to project from substantially the center, in the width direction Y, of the edge 212 of the heating connection end 211.

The lead connection end 221 of the lead portion 22 has the edge 222 having a convex part 223 which is configured similar to the convex part 213.

When the convex parts 213, 223 have a length S (S1, S2) in the long direction X and each of the joints 23 excluding the convex parts 213, 223 has a length M in the long direction X, the relation of S=a×M+b is realized, where "a" ranges from 0.3 mm to 5.0 mm, and "b" ranges from 0.0 mm to 0.2 mm.

Since the configuration other than the above is similar to that of the first example, explanations are omitted.

According to the present example, in manufacturing the ceramic heater 1, even when there is an offset in the formation position of the heating element 21 and the lead portions 22 in the long direction X, a sufficient joint area is secured between the heating element 21 and each of the lead portions 22. As a result, it may prevent abnormal generation of heat at the joints 23 and the occurrence of the crack starting at the joints 23.

The function, and effect other than the above of the third example are similar to those of the ceramic heater 1 according to the first example.

While there has been described what is at present considered to be these examples of the invention, it will be understood that various examples which are not described yet may be made therein, and it is intended to cover all claims within the true spirit and scope of the invention.

What is claimed is:

1. A ceramic heater that is formed by providing a heater pattern on a ceramic substrate, the heater pattern having a heat generation portion for generating heat when current is passed therethrough and a pair of lead portions for supplying current to the heat generation portion, the ceramic heater being characterized in that:
the heat generation portion has a pair of heat generation connecting ends that are connected to the pair of lead portions;
the lead portions have respective lead connecting ends that are connected to the respective heat generation connecting ends of the heat generation portion;
the heat generation portion and the lead portions are connected to each other in connecting portions in each of which the heat generation connecting end overlaps with the corresponding lead connecting end;
when the ceramic substrate is viewed from a direction perpendicular to a surface in which the heater pattern is formed, the heater pattern is in a shape having sides in a width direction of each connecting portion, each side having an intersection portion in which a contour of the heat generation connecting end of the heat generation portion intersects a contour of the lead connecting end of the corresponding lead portion to form a concave portion in which the heater pattern is recessed inward;
at least one of the heat generation connecting end of the heat generation portion and the lead connecting end of the lead portion in the shape of the heater pattern has an edge that is an arc-shaped curve.

2. The ceramic heater according to claim 1, characterized in that a relation R1≤R2 is established, where R1 is a resistance of a connecting area having a length L from a tip of the lead connecting end of each lead portion to a tip of the heat generation connecting end of the heat generation portion in a longitudinal direction of the heater pattern, and R2 is a resistance of a lead area extending, by the length L, from the tip of the heat generation connecting end of the heat generation portion toward the lead portion.

3. The ceramic heater according to claim 1, characterized in that at least one of the heat generation connecting end of the heat generation portion and the lead connecting end of each lead portion in the shape of the heater pattern has an edge provided with a convex portion projected in a longitudinal direction of the heater pattern.

4. The ceramic heater according to claim 3, characterized in that a relation S=a×M+b is established, where S is a length of the convex portion in the longitudinal direction, M is a length of the connecting portion in the longitudinal direction excluding the convex portion, a=0.3 to 5 and b=0 to 0.2 mm.

5. The ceramic heater according to claim 1, characterized in that the connecting portion is formed by laying the lead connecting end of each lead portion over the heat generation connecting end of the heat generation portion, and the lead connecting end has a width smaller than that of the heat generation connecting end.

6. The ceramic heater according to claim 1, characterized in that the heat generation portion contains platinum, gold, palladium, rhenium or a mixture of these components as a main component, and contains 11 to 14 parts by weight of alumina, zirconia, titania or a mixture of these components when a content of the main component is 100 parts by weight.

7. The ceramic heater according to claim 1, characterized in that each lead portion contains platinum, gold, palladium, rhenium or a mixture of these components as a main component, and contains 7 to 10 parts by weight of alumina, zirconia, titania or a mixture of these components when a content of the main component is 100 parts by weight.

8. The ceramic heater according to claim 1, characterized in that the heater pattern is formed by printing a conductive paste.

9. A gas sensor element characterized in that the gas sensor element comprises the ceramic heater recited in claim 1.

* * * * *